United States Patent
Li et al.

(10) Patent No.: US 12,345,695 B2
(45) Date of Patent: Jul. 1, 2025

(54) PREPARATION METHOD AND APPLICATION OF FLEXIBLE PAPER-BASED SENSOR FOR DETECTING MEAT PRODUCTS

(71) Applicant: JIANGSU UNIVERSITY, Zhenjiang (CN)

(72) Inventors: Huanhuan Li, Zhenjiang (CN); Qiyi Bei, Zhenjiang (CN); Jiayu Gao, Zhenjiang (CN); Wei Sheng, Zhenjiang (CN); Quansheng Chen, Zhenjiang (CN); Wei Zhang, Zhenjiang (CN); Yu Wu, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 0 days.

(21) Appl. No.: 19/031,722

(22) Filed: Jan. 18, 2025

(65) Prior Publication Data
US 2025/0164455 A1    May 22, 2025

Related U.S. Application Data

(63) Continuation of application No. PCT/CN2024/141333, filed on Dec. 23, 2024.

(30) Foreign Application Priority Data

May 29, 2024    (CN) .......................... 202410678226.0

(51) Int. Cl.
*G01N 33/12*    (2006.01)
*G01N 33/543*    (2006.01)

(52) U.S. Cl.
CPC ....... *G01N 33/12* (2013.01); *G01N 33/54366* (2013.01); *G01N 2430/00* (2013.01)

(58) Field of Classification Search
CPC ............. G01N 33/12; G01N 33/54366; G01N 2430/00
See application file for complete search history.

(56) References Cited

FOREIGN PATENT DOCUMENTS

| | | | |
|---|---|---|---|
| CN | 113310956 A | * 8/2021 | ........... G01N 21/643 |
| CN | 115144388 A | 10/2022 | |
| CN | 116609406 A | * 8/2023 | |
| CN | 117929331 A | * 4/2024 | |
| WO | 2023037286 A1 | 3/2023 | |

OTHER PUBLICATIONS

Ouyang et al , "Rapid and specific sensing of tetracycline in food using a novel upconversion aptasensor" Food Control 81 (2017) 156-163 (Year: 2017).*

Yu et al "Functionalized MIL-53(Fe) as efficient adsorbents for removal of tetracycline antibiotics from aqueous solution" Microporous and Mesoporous Materials, vol. 290, Dec. 2019, 109642 (Year: 2019).*

* cited by examiner

*Primary Examiner* — Dennis White (57) ABSTRACT

A flexible paper-based sensor for detecting meat products is provided, which is prepared through steps of mixing a UCNPs-cDNA signal probe with an Apt-MIL-53(Fe)@$Cu^{2+}$ capture probe to prepare a detection probe; and dropwise adding the detection probe onto a central area of a paper-based substrate to obtain the flexible paper-based sensor. A method for detecting tetracycline residues in meat products using such sensor is also provided.

7 Claims, 7 Drawing Sheets

Specification includes a Sequence Listing.

SEQUENCE LISTING

```
Sequence total quantity: 2
SEQ ID NO: 1            moltype = DNA   length = 76
FEATURE                 Location/Qualifiers
source                  1..76
                        mol_type = other DNA
                        organism = synthetic construct
SEQUENCE: 1
cgtacggaat tcgctagccc cccggcaggc cacggcttgg gttggtccca ctgcgcgtgg  60
atccgagctc cacgtg                                                  76

SEQ ID NO: 2            moltype = DNA   length = 76
FEATURE                 Location/Qualifiers
source                  1..76
                        mol_type = other DNA
                        organism = synthetic construct
SEQUENCE: 2
gcatgcctta agcgatcggg gggccgtccg gtgccgaacc caaccagggt gacgcgcacc  60
taggctcgag gtgcac                                                  76
```

PREPARATION METHOD AND APPLICATION OF FLEXIBLE PAPER-BASED SENSOR FOR DETECTING MEAT PRODUCTS

REFERENCE TO AN ELECTRONIC SEQUENCE LISTING

The contents of the electronic sequence listing (Name: SequenceListing.xml; Size: 2,691 bytes; and Date of Creation: May 28, 2024) is herein incorporated by reference in its entirety.

CROSS-REFERENCE TO RELATED APPLICATIONS

This application is a continuation of International Patent Application No. PCT/CN2024/141333, filed on Dec. 23, 2024, which claims the benefit of priority from Chinese Patent Application No. 202410678226.0, filed on May 29, 2024. The content of the aforementioned application, including any intervening amendments thereto, is incorporated herein by reference in its entirety.

TECHNICAL FIELD

This application relates to antibiotic detection technologies, and more particularly to a preparation method and an application of a flexible paper-based sensor for detecting meat products.

BACKGROUND

Tetracycline is a commonly used antibiotic for treating fish diseases in the aquaculture. However, due to the insufficient understanding of pathogens and antibiotics, the misuse or overuse of tetracycline frequently occurs, resulting in the residue in fish. The tetracycline residues in fish will accumulate gradually in the human body through the food chain, posing significant health risks and potentially leading to various health issues such as tooth discoloration, liver damage, gastrointestinal disorders and allergic reactions. Traditional methods for detecting tetracycline residues include High-Performance Liquid Chromatography (HPLC), Capillary Electrophoresis (CE), Enzyme-Linked ImmunoSorbent Assay (ELISA) and Liquid Chromatography-Mass Spectrometry (LC-MS). While these methods offer high detection accuracy and reliable results, they have evident drawbacks, such as complex procedures and long detection times. In this regard, there is an urgent need to develop a rapid and highly sensitive method for detecting tetracycline residues in fish, which can meet the practical requirements for on-site rapid detection of tetracycline residues in fish.

SUMMARY

An object of the disclosure is to provide a preparation method and an application of a flexible paper-based sensor for detecting tetracycline residues in meat products to overcome the defects in the prior art. The flexible paper-based sensor provided herein is portable and capable of accurately identifying tetracycline, enabling rapid and on-site sensitive detection of tetracycline in meat products.

Technical solutions of the present disclosure are described as follows.

In a first aspect, this application provides a flexible paper-based sensor for detecting tetracycline residues in meat products, wherein the flexible paper-based sensor is prepared through steps of:

(1) dissolving yttrium chloride hexahydrate, ytterbium chloride hexahydrate and erbium chloride hexahydrate in a first solvent, followed by addition of oleic acid and 1-octadecene, a first reaction under heating and stirring, and cooling to obtain a first mixture, wherein the first solvent is methanol;

dissolving ammonium fluoride and sodium hydroxide in a second solvent to produce a solution, wherein the second solvent is methanol; mixing the solution with the first mixture followed by a second reaction under heating and stirring, injection of nitrogen gas, a third reaction under heating and stirring in a nitrogen atmosphere, and cooling to obtain a second mixture; and subjecting the second mixture to washing, centrifugation and drying to obtain an upconversion fluorescent nanomaterial; and mixing the upconversion fluorescent nanomaterial with chloroform, toluene and a polyacrylic acid aqueous solution followed by a fourth reaction under stirring, centrifugation and drying to obtain a carboxylated upconversion nanomaterial;

(2) adding a 1-ethyl-(3-dimethylaminopropyl) carbodiimide hydrochloride aqueous solution and a N-hydroxysulfosuccinimide aqueous solution to the carboxylated upconversion nanomaterial to obtain an incubation system; incubating the incubation system under shaking, followed by addition of a solution of a complementary chain of a tetracycline aptamer under shaking to obtain a UCNPs-cDNA signal probe;

(3) dissolving 2-aminoterephthalic acid and $Fe(NO_3)_3 \cdot 9H_2O$ in N, N-dimethylformamide under stirring, followed by a fifth reaction in a reactor, centrifugal washing and drying to obtain $NH_2$-MIL (abbreviation of Material from Institute Lavoisier)-53(Fe);

dissolving $NH_2$-MIL-53(Fe) and $CuCl_2$ in deionized water followed by a sixth reaction under stirring to obtain $NH_2$-MIL-53(Fe)@$Cu^{2+}$;

adding a glutaraldehyde solution and a phosphate-buffered saline (PBS) to $NH_2$-MIL-53(Fe)@$Cu^{2+}$ followed by shaking in the dark, and centrifugation to collect a precipitate; and adding the tetracycline aptamer to the precipitate followed by shaking overnight and centrifugation to obtain an Apt-MIL-53(Fe)@$Cu^{2+}$ capture probe;

(4) mixing the UCNPs-cDNA signal probe with the Apt-MIL-53(Fe)@$Cu^{2+}$ capture probe to obtain a detection probe; and (5) dropwise adding the detection probe onto a central area of a paper-based substrate to obtain the flexible paper-based sensor.

In some embodiments, in step (1), a ratio of the yttrium chloride hexahydrate to the ytterbium chloride hexahydrate to the erbium chloride hexahydrate to the first solvent to oleic acid to 1-octadecene is (220-250) mg:(70-80) mg:(5-10) mg:(6-10) mL:(6-10) mL:(15-20) mL; a ratio of ammonium fluoride to sodium hydroxide to the second solvent is (0.1-0.2) g:(0.1-0.15) g: 10 mL; a ratio of the upconversion fluorescent nanomaterial to chloroform to toluene to the polyacrylic acid aqueous solution is 25 mg: 2 mL: 3 mL: 10 mL; and the first reaction is carried out at 160-170° C. under stirring at 300-500 rpm for 25-40 min; the second reaction is carried out at 50-70° C. under stirring at 300-500 rpm for 70-100 min; and the third reaction is carried out at 290-300° C. under stirring at 300-500 rpm for 60-90 min.

In some embodiments, in step (2), a ratio of the carboxylated upconversion nanomaterial to the 1-ethyl-(3-dimethylaminopropyl) carbodiimide hydrochloride aqueous solution to the N-hydroxysulfosuccinimide aqueous solution to the solution of the complementary chain is 20 mg: 1 mL: 1 mL: 60 μL; and the complementary chain consists of a sequence shown as 5'-GCATGCCTTAAGC-GATCGGGGGGCCGTCCGGTGCCGAACC-CAACCAGGGT GACGCGCACCTAGGCTCGAGGTGCAC-$C_6$—$NH_2$-3' (SEQ ID NO:2).

In some embodiments, in step (3), a ratio of 2-aminoterephthalic acid to $Fe(NO_3)_3 \cdot 9H_2O$ to N,N-dimethylformamide is (0.9-1.0) g:(2.0-2.1) g: 50 mL;

a ratio of the $NH_2$-MIL-53(Fe) to $CuCl_2$ to the deionized water is 50 mg: 1 g: 10 mL;

a ratio of the $NH_2$-MIL-53(Fe)@$Cu^{2+}$ to the glutaraldehyde solution to the PBS to the tetracycline aptamer is 10 mg: 1.25 mL: 5 mL: 30 μL;

the tetracycline aptamer consists of a sequence shown as 5'-$NH_2C_6$-CGTACGGAAT-TCGCTAGCCCCCCGGCAGGC-CACGGCTTGGGTTGGTCCCAC TGCGCGTG-GATCCGAGCTCCACGTG-3' (SEQ ID NO:1); and the fifth reaction is carried out in the reactor at 150-160° C. for 7-9 h, and the sixth reaction is carried out for 10-12 h.

In some embodiments, in step (4), a volume ratio of the UCNPs-cDNA signal probe to the Apt-MIL-53(Fe)@$Cu^{2+}$ capture probe is 1:1; a concentration of the UCNPs-cDNA signal probe is 2 mg/mL, and a concentration of the Apt-MIL-53(Fe)@$Cu^{2+}$ capture probe is 1.2 mg/mL; and the mixing is carried out for 15 min.

In some embodiments, in step (5), an addition amount of the detection probe is 3.5 μL; and the paper-based substrate is prepared through steps of:
ultrasonically mixing ethanol, ammonia water and tetraethyl orthosilicate to obtain a mixed solution, adding a cleaned filter paper to the mixed solution followed by shaking on a shaker, addition of 3-aminopropyltrimethoxysilane, reaction under shaking, washing and drying to obtain a silica-modified filter paper; and subjecting the silica-modified filter paper to hydrophobization to obtain the paper-based substrate.

In a second aspect, this application provides a method for detecting tetracycline residues in a meat product, comprising:

adding a test sample to the flexible paper-based sensor described above, detecting a fluorescence intensity characteristic value of the test sample, and substituting the fluorescence intensity characteristic value into a tetracycline detection standard curve to calculate a tetracycline content in the test sample.

In some embodiments, a linear regression equation of the tetracycline detection standard curve is y=1873.01x−425.34.

In a third aspect, this application provides an application of the flexible paper-based sensor disclosed herein in the preparation of detection products for tetracycline residues in meat products.

In some embodiments, the meat product includes fish meat.

Compared to the prior art, the present disclosure has the following beneficial effects.

(1) The present disclosure provides the flexible paper-based sensor for detecting tetracycline residues in meat products. Filter paper is used as a substrate, making the sensor provided herein portable. Silicon dioxide microspheres are modified on a surface of the filter paper to increase its specific surface area, which is beneficial for loading more detection probes and can improve the detection sensitivity.

(2) Apt-MIL-53(Fe)@$Cu^{2+}$ synthesized herein functions as an effective quencher, efficiently quenching the fluorescence of UCNPs-cDNA through fluorescence resonance energy transfer (FRET), thereby enhancing detection efficiency. Used as a capture probe, Apt-MIL-53(Fe)@$Cu^{2+}$ enables the flexible paper-based sensor to achieve high specificity and anti-interference capability through the specific recognition of tetracycline by the Apt on the capture probe surface, ensuring accurate identification and improved detection accuracy.

(3) The present disclosure utilizes the ability of $Cu^{2+}$ to bind with tetracycline to form a stable tetracycline-Cu complex, enhancing the detection sensitivity. In the presence of tetracycline, $Cu^{2+}$ on the surface of the capture probe can bind with the tetracycline. Due to the negative potential on the capture probe, signal probe and the tetracycline, the binding of tetracycline to the capture probe further increases the negative charge on Apt-MIL-53(Fe)@$Cu^{2+}$, preventing the capture and signal probes from reconnecting through electrostatic adsorption after separation. The described interaction effectively improves the sensitivity and accuracy of the sensor.

(4) Apt-MIL-53(Fe)@$Cu^{2+}$ prepared herein can bind with UCNPs-cDNA to detect tetracycline residues in actual samples. A 1.2 mg/mL Apt-MIL-53(Fe)@$Cu^{2+}$ solution and a 2 mg/mL UCNPs-cDNA solution are precisely mixed in a volume ratio of 1:1 to prepare the detection probe, so as to improve the detection sensitivity and reliability. Moreover, the detection method disclosed herein is simple to operate, enabling rapid and on-site sensitive detection of tetracycline in meat products.

BRIEF DESCRIPTION OF THE DRAWINGS

In order to illustrate the technical solutions in the embodiments of the present disclosure or the prior art more clearly, the accompanying drawings needed in the description of the embodiments will be briefly described below. Obviously, presented in the accompanying drawings are only some embodiments of the present disclosure, and for those of ordinary skill in the art, other accompanying drawings can be obtained from the structures illustrated therein without making creative effort.

DETAILED DESCRIPTION OF EMBODIMENTS

Various exemplary embodiments of the present disclosure will be described in detail herein. Such detailed descriptions should not be construed as a limitation on the present disclosure but rather as a more specific explanation of certain aspects, features and implementations thereof.

It should be understood that the terms described herein are provided solely for illustrating specific embodiments and are not intended to limit the present disclosure. Additionally, any numerical ranges disclosed herein are to be understood as explicitly including every intermediate value between their upper and lower limits. Furthermore, all smaller ranges defined by intermediate values within any stated value or range, or between other stated values, are also included. The upper and lower limits of these smaller ranges may independently be included or excluded.

Unless otherwise stated, all technical and scientific terms used herein have the same meaning as commonly understood by those skilled in the art relevant to the present disclosure. While preferred methods and materials are described, any similar or equivalent methods and materials may also be used in the implementation or testing of the present disclosure. All references cited herein are incorporated by reference to disclose and describe methods and/or materials related to those references. In case of any conflict, the content of this specification shall prevail.

Various modifications and variations of the embodiments described herein can be made without departing from the scope or spirit of the present disclosure, which will be apparent to those skilled in the art. Other embodiments obtained from the present disclosure are also obvious to those skilled in the art. The description and embodiments provided herein are merely illustrative.

As used herein, terms such as "comprise", "include", "have" and "contain" are open-ended expressions, meaning "including but not limited to".

Example 1

Figure 1:
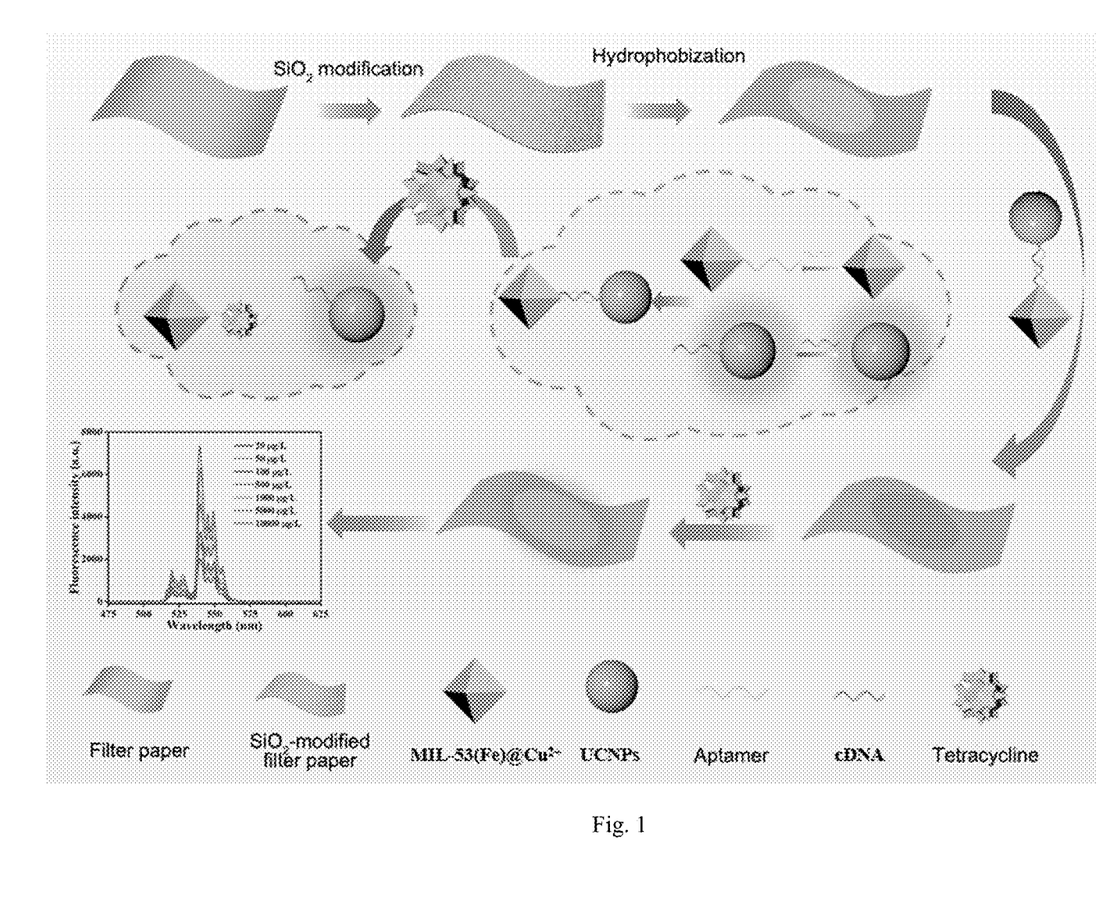
FIG. 1 is a preparation flowchart of a flexible paper-based sensor according to an embodiment of the present disclosure.

To further verify the detection effect of a flexible paper-based sensor (FIG. 1 illustrated a preparation flowchart of the flexible paper-based sensor) and a detection method provided herein for tetracycline residues in meat products, the detection of tetracycline in fish was taken as an example. The detection method was performed as follows.

Figure 2:
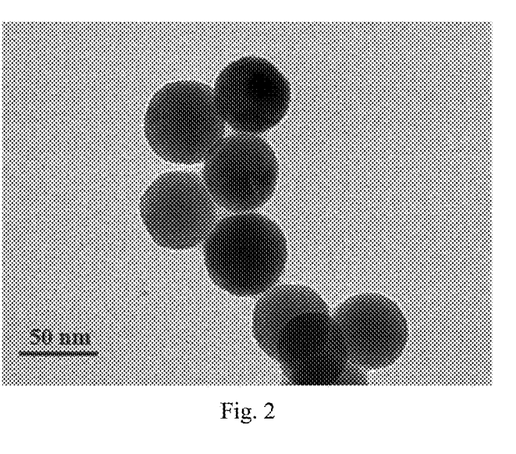
FIG. 2 is a transmission electron microscope image of an upconversion fluorescent nanomaterial according to an embodiment of the present disclosure.

(1) 236.6 mg of yttrium chloride hexahydrate, 77.5 mg of ytterbium chloride hexahydrate and 7.6 mg of erbium chloride hexahydrate were dissolved in 6 mL of methanol, to which 6 mL of oleic acid and 15 mL of 1-octadecene were added. Nitrogen gas was injected into the reaction mixture, followed by a first reaction under heating and stirring in a nitrogen atmosphere. The first reaction was carried out at 160° C. under stirring at 400 rpm for 30 min. After the reaction was completed, the reaction mixture was cooled to room temperature to produce a mixed solution A. 0.1482 g of ammonium fluoride and 0.1 g of sodium hydroxide were dissolved in 10 mL of methanol to obtain a solution. The solution was mixed with the mixed solution A, followed by a second reaction under heating and stirring, injection of nitrogen gas, a third reaction under heating and stirring in a nitrogen atmosphere, and cooling to obtain a mixed solution B. The second reaction was carried out at 70° C. under stirring for 90 min. The third reaction was carried out at 300° C. for 80 min. The mixed solution B was subjected to washing using a mixture of ethanol and cyclohexane, centrifugation and drying to yield an upconversion fluorescent nanomaterial (as shown in FIG. 2). The nanomaterial obtained herein was uniformly dispersed with a consistent diameter of approximately 50 nm.

50.0 mg of the upconversion fluorescent nanomaterial was ultrasonically mixed with 6.0 mL of toluene and 4.0 mL of chloroform in a round-bottomed flask. The reaction mixture was reacted with 20.0 mL of a 15 mg/mL polyacrylic acid aqueous solution in the dark under stirring for 48 h, followed by centrifugation and washing to remove excess polyacrylic acid to yield a carboxylated upconversion nanomaterial.

(2) 10 mg of the carboxylated upconversion nanomaterial was dissolved in 10 mL of MES (2-morpholinoethanesulphonic acid) buffer, to which 0.5 mL of a 1 mg/mL N-hydroxysulfosuccinimide aqueous solution and 0.5 mL of a 2 mg/mL 1-ethyl-(3-dimethylaminopropyl) carbodiimide hydrochloride aqueous solution were added to obtain an incubation system. Then the incubation system was incubated under shaking for 2 h, followed by addition of 30 μL of a solution of a complementary chain of a tetracycline aptamer at 100 μM under shaking for 12 h. The tetracycline aptamer and its complementary chain were purchased from Sangon Biotech (Shanghai) Co., Ltd.

Figure 3:
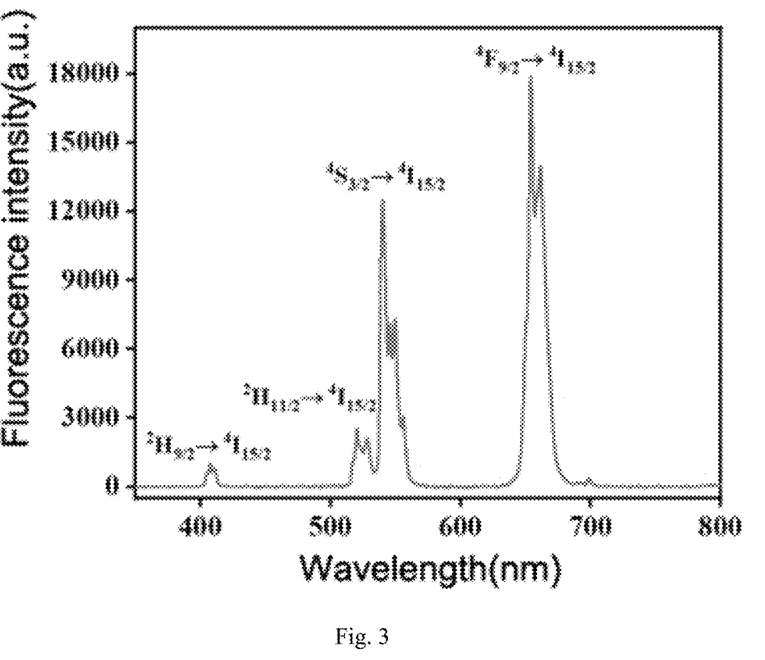
FIG. 3 is a fluorescence spectrum of UCNPs-cDNA according to an embodiment of the present disclosure.

The tetracycline aptamer consisted of a sequence shown as 5'-$NH_2C_6$-CGTACGGAAT-TCGCTAGCCCCCCGGCAGGC-CACGGCTTGGGTTGGTCCCAC TGCGCGTG-GATCCGAGCTCCACGTG-3' (SEQ ID NO:1). The complementary chain consisted of a sequence shown as 5'-GCATGCCTTAAGC-GATCGGGGGGCCGTCCGGTGCCGAACC-CAACCAGGGT GACGCGCACCTAGGCTCGAGGTGCAC-$C_6$—$NH_2$-3' (SEQ ID NO:2). Then the reaction mixture was subjected to centrifugation and washing to remove surface impurities, and resuspended in 5 mL of phosphate-buffered saline (PBS) to yield UCNPs-cDNA as a signal probe. The signal probe provided herein exhibited excellent luminescent properties, effectively reducing background fluorescence interference and enhancing the detection accuracy (as shown in FIG. 3).

Figure 4:
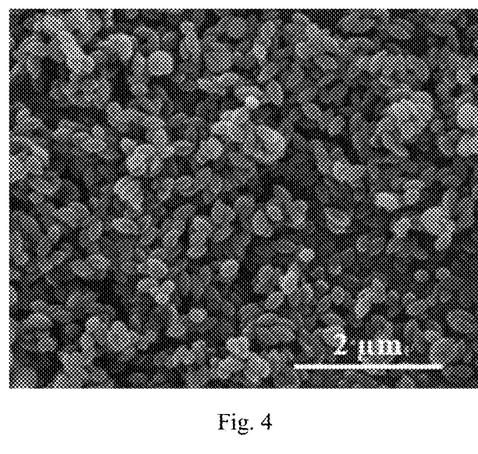
FIG. 4 is a transmission electron microscope image of $NH_2$-MIL-53(Fe) according to an embodiment of the present disclosure.

(3) 0.905 g of 2-aminoterephthalic acid and 2.02 g of $Fe(NO_3)_3 \cdot 9H_2O$ were dissolved in 50 mL of N,N-dimethylformamide under stirring for 10 min to ensure uniform dispersion. Then the reaction mixture was transferred to a high-pressure reactor, followed by a fourth reaction at 150° C. for 8 h, cooling to room temperature, centrifugation at 6,000 rpm for 5 min to collect a first precipitate. The first precipitate was subjected to washing with N,N-dimethylformamide and ethanol absolute and drying at 60° C. for 12 h to yield a brown product $NH_2$-MIL-53(Fe) (as shown in FIG. 4). The $NH_2$-MIL-53(Fe) obtained herein had an olive-shaped structure with smooth surfaces and intact morphology. The nanoparticle was uniform in size, with an average particle size of approximately 410 nm, and exhibited a large pore volume and high specific surface area, which were beneficial for the adsorption of $Cu^{2+}$. 100 mg of $NH_2$-MIL-53(Fe) and 2 g of $CuCl_2$ were dissolved in 20 mL of water under stirring for 10 h followed by centrifugal washing to obtain $NH_2$-MIL-53(Fe)@$Cu^{2+}$. 10 mg of $NH_2$-MIL-53(Fe)@$Cu^{2+}$ was added with 1.25 mL of a glutaraldehyde solution and 5 mL of PBS, followed by a fifth reaction at 25° C. under shaking in the dark for 2 h and centrifugation to obtain a second precipitate. The second precipitate was washed three times and reacted with 5 mL of PBS and 30 µL of 100 M tetracycline aptamer at 37° C. under gentle shaking overnight. Then the reaction mixture was centrifuged to collected a third precipitate, and the third precipitate was washed with PBS and resuspended in PBS to yield an Apt-MIL-53(Fe)@$Cu^{2+}$ solution, serving as a capture probe.

(4) A 2 mg/mL UCNPs-cDNA solution and a 1.2 mg/mL Apt-MIL-53(Fe)@$Cu^{2+}$ solution were mixed at a volume ratio of 1:1 and incubated at 37° C. to obtain a detection probe.

(5) Whatman No. 1 qualitative filter paper was cut into equal-sized pieces, soaked in 0.1 mol/L HCl for 30 min, washed with deionized water and dried in a drying oven at 50° C. to obtain a cleaned filter paper. Then, 20 mL of 80% ethanol, 500 µL of ammonia water and 300 µL of tetraethyl orthosilicate (TEOS) were ultrasonically mixed, followed by addition of the cleaned filter paper. The resulting mixture was reacted in a water bath under shaking at 40° C. for 8 h. Then, 300 µL of 3-aminopropyltrimethoxysilane (APTES) was added, and the reaction was continued to perform under shaking for 2 h. After the reaction was completed, the resulting filter paper was washed three times with deionized water and ethanol absolute, respectively, followed by drying at 50° C. for 1 h to obtain a silica-modified filter paper. The edges of the silica-modified filter paper were subjected to hydrophobization. A pattern was designed on a computer and printed onto the silica-modified filter paper using an inkjet printer. The printed filter paper was processed in an oven at 200° C. for 6 h to allow the toner to permeate the filter paper fibers, forming hydrophobic regions on the surface. After natural cooling, a paper-based substrate was obtained and stored in a dry environment for later use.

(6) 3.5 µL of the detection probe was dropwise added onto a central area of the paper-based substrate to prepare a flexible paper-based sensor. The sensor provided herein was compact, portable, easy to use and suitable for on-site detection applications.

Figure 5:
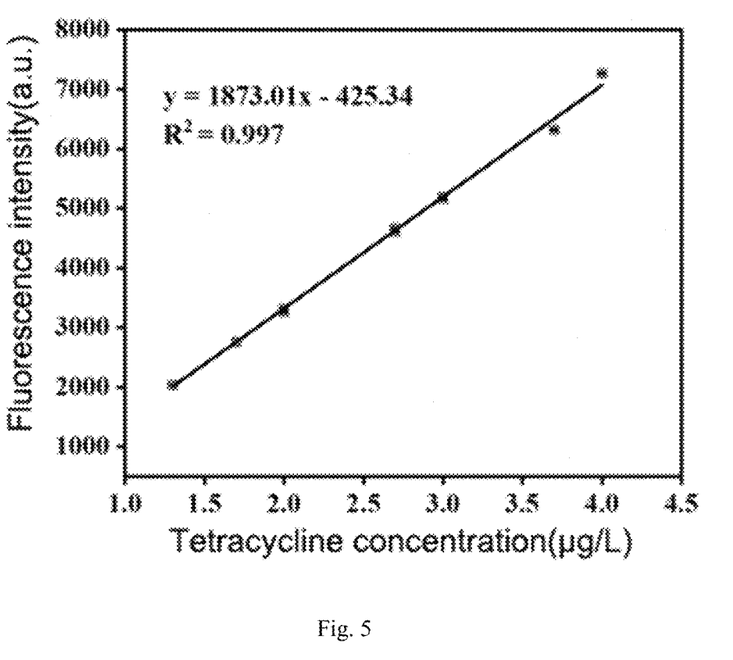
FIG. 5 is a fluorescence standard curve for tetracycline at different concentrations according to an embodiment of the present disclosure.
Figure 6:
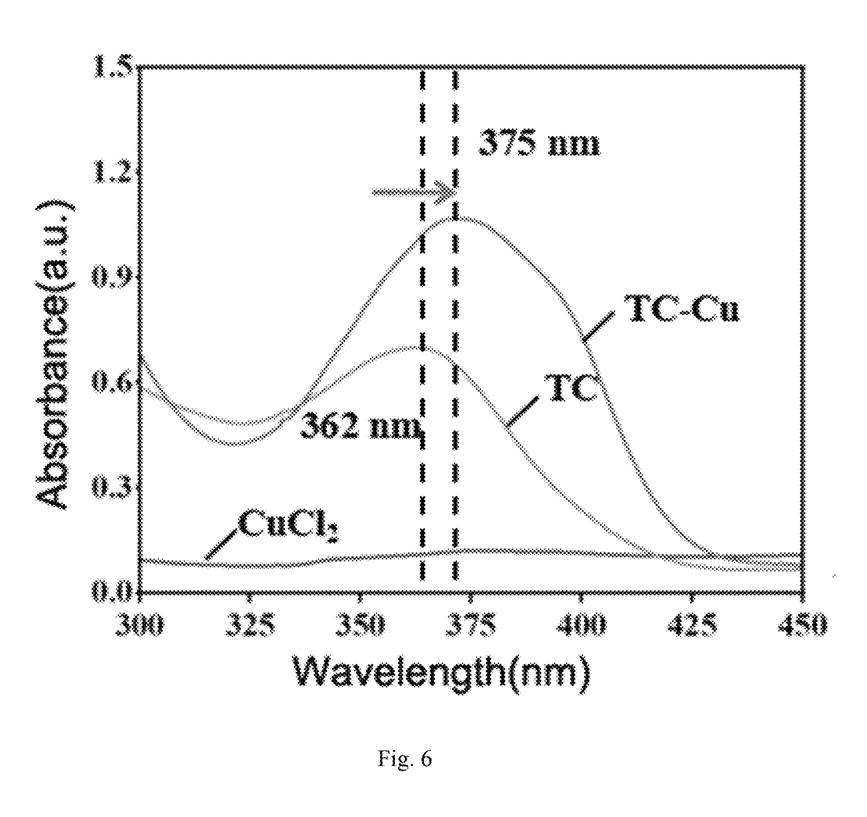
FIG. 6 is a detection result of a complexation reaction between tetracycline (TC) and $Cu^{2+}$ according to an embodiment of the present disclosure.
Figure 7:
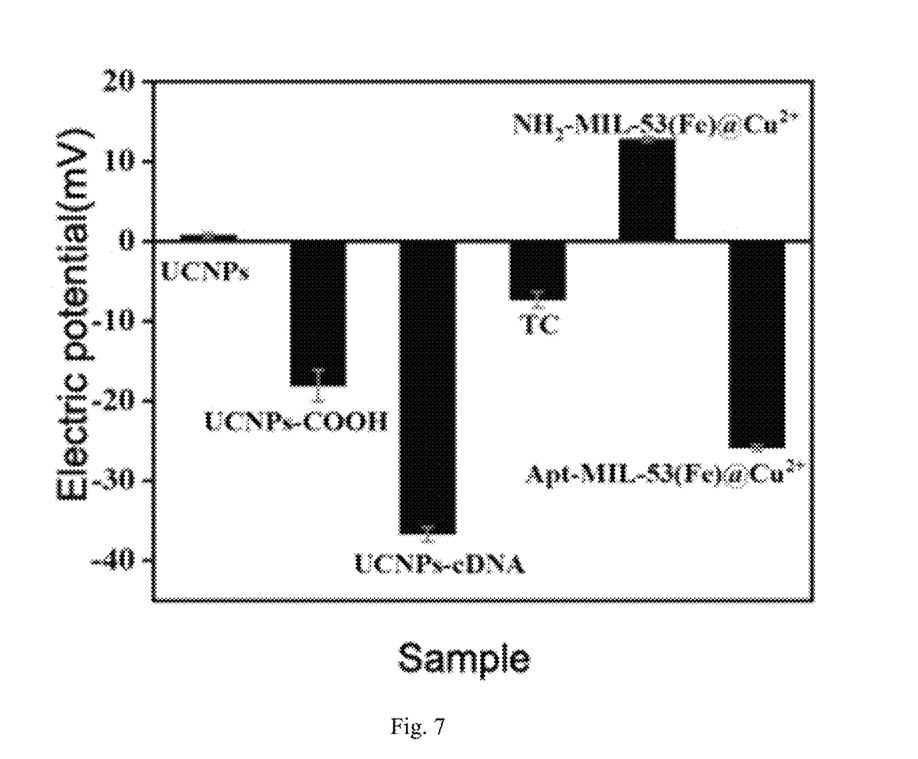
FIG. 7 is an electric potential result of tetracycline (TC), a signal probe and a capture probe according to an embodiment of the present disclosure.

(7) Tetracycline standard solutions of different concentrations (20, 50, 100, 500, 1000, 5000, 10000 µg/L) were prepared. Different concentrations of the tetracycline standard solutions were added to the flexible paper-based sensor to detect the fluorescence intensity of the sensor. Based on the fluorescence intensity corresponding to different concentrations of the tetracycline standard solutions, a tetracycline detection standard curve was plotted with the logarithm of the tetracycline concentration as the x-axis and the fluorescence intensity signal characteristic values as the y-axis (shown in FIG. 5). The detection limit of this curve is 1.18 µg/L and the detection range is 20-10,000 µg/L. Tetracycline can specifically bind to the tetracycline aptamer (Apt) on the surface of the capture probe and simultaneously undergo a complexation reaction with $Cu^{2+}$ (as shown in FIG. 6). This reaction enhanced the negative charge of the capture probe (as shown in FIG. 7), further separating the capture probe from the signal probe, thereby enhancing the accuracy and sensitivity of the detection.

(8) 5 g of fish meat sample was mixed with different concentrations of the tetracycline standard solutions and 20 mL of EDTA·2Na-McIlvaine buffer, and vortexed for 10 min. The reaction mixture was added with 5 mL of a 18.5% $H_2SO_4$ solution and 5 mL of a 70 mg/mL sodium tungstate solution and vortexed for 1 min followed by centrifugation to collect a first supernatant and a fourth precipitate. The fourth precipitate was extracted twice with EDTA·2Na-McIlvaine buffer to obtain a second supernatant and a third supernatant. Then the first, second and third supernatants were mixed followed by a first filtration through a filter paper to remove large particulate impurities and a second filtration through a 0.22 m micropore filter to obtain a sample solution. 3.5 µL of the sample solution was then added to the flexible paper-based sensor to measure the fluorescence intensity signal characteristic value. The fluorescence intensity signal characteristic value was substituted into the tetracycline detection standard curve obtained above to calculate the tetracycline content in the fish meat sample.

Three fish meat samples were tested for tetracycline content using the method and steps described herein and the results were verified using the national standard method. The measurement results were shown in Table 1. It can be concluded that the method disclosed herein demonstrated good accuracy in actual samples, indicating a promising application prospect.

Table 1 Results of Detecting Tetracycline Content in Fish Meat Samples Using the Method Provided Herein and High-Performance Liquid Chromatography (HPLC)

| | HPLC | | Method provided herein | | |
| --- | --- | --- | --- | --- | --- |
| Sample | Detected concentration (µg/kg) | Relative standard deviation (%) | Detected concentration (µg/kg) | Relative standard deviation (%) | t-test |
| Fish meat | 3950.54 ± 9.92 | 0.25 | 3957.92 ± 235.14 | 5.94 | P > 0.05 |
| | 891.73 ± 6.44 | 0.72 | 871.36 ± 6.83 | 0.78 | |
| | 423.88 ± 3.11 | 0.74 | 414.74 ± 8.36 | 2.02 | |

Described above are merely preferred embodiments of the present disclosure, and are not intended to limit the scope of the present disclosure. It should be understood that various modifications, changes and replacements made by those skilled in the art without departing from the spirit of the disclosure shall fall within the scope of the present disclosure defined by the appended claims.

What is claimed is:

1. A flexible paper-based sensor for detecting tetracycline residues in meat products, wherein the flexible paper-based sensor is prepared through steps of:

(1) dissolving yttrium chloride hexahydrate, ytterbium chloride hexahydrate and erbium chloride hexahydrate in a first solvent, followed by addition of oleic acid and 1-octadecene, a first reaction under heating and stirring, and cooling to obtain a first mixture, wherein the first solvent is methanol;

dissolving ammonium fluoride and sodium hydroxide in a second solvent to produce a solution, wherein the second solvent is methanol; mixing the solution with the first mixture followed by a second reaction under heating and stirring, injection of nitrogen gas, a third reaction under heating and stirring in a nitrogen atmosphere, and cooling to obtain a second mixture; and subjecting the second mixture to washing, centrifugation and drying to obtain an upconversion fluorescent nanomaterial; and mixing the upconversion fluorescent nanomaterial with chloroform, toluene and a polyacrylic acid aqueous solution followed by a fourth reaction under stirring, centrifugation and drying to obtain a carboxylated upconversion nanomaterial;

(2) adding a 1-ethyl-(3-dimethylaminopropyl) carbodiimide hydrochloride aqueous solution and a N-hydroxysulfosuccinimide aqueous solution to the carboxylated upconversion nanomaterial to obtain an incubation system; incubating the incubation system under shaking, followed by addition of a solution of a complementary chain of a tetracycline aptamer under shaking to obtain a UCNPs-cDNA signal probe;

(3) dissolving 2-aminoterephthalic acid and $Fe(NO_3)_3 \cdot 9H_2O$ in N, N-dimethylformamide under stirring, followed by a fifth reaction in a reactor, centrifugal washing and drying to obtain $NH_2$-MIL-53(Fe);

dissolving $NH_2$-MIL-53(Fe) and $CuCl_2$ in deionized water followed by a sixth reaction under stirring to obtain $NH_2$-MIL-53(Fe)@$Cu^{2+}$;

adding a glutaraldehyde solution and a phosphate-buffered saline (PBS) to $NH_2$-MIL-53(Fe)@$Cu^{2+}$ followed by shaking in the dark, and centrifugation to collect a precipitate; and adding the tetracycline aptamer to the precipitate followed by shaking overnight and centrifugation to obtain an Apt-MIL-53(Fe)@$Cu^{2+}$ capture probe;

(4) mixing the UCNPs-cDNA signal probe with the Apt-MIL-53(Fe)@$Cu^{2+}$ capture probe to obtain a detection probe; and (5) dropwise adding the detection probe onto a central area of a paper-based substrate to obtain the flexible paper-based sensor;

wherein in step (1), a ratio of the yttrium chloride hexahydrate to the ytterbium chloride hexahydrate to the erbium chloride hexahydrate to the first solvent to oleic acid to 1-octadecene is (220-250) mg:(70-80) mg:(5-10) mg:(6-10) mL:(6-10) mL:(15-20) mL;

a ratio of ammonium fluoride to sodium hydroxide to the second solvent is (0.1-0.2) g:(0.1-0.15) g: 10 mL;

a ratio of the upconversion fluorescent nanomaterial to chloroform to toluene to the polyacrylic acid aqueous solution is 25 mg: 2 mL: 3 mL: 10 mL; and the first reaction is carried out at 160-170° C. under stirring at 300-500 rpm for 25-40 min; the second reaction is carried out at 50-70° C. under stirring at 300-500 rpm for 70-100 min; and the third reaction is carried out at 290-300° C. under stirring at 300-500 rpm for 60-90 min.

2. The flexible paper-based sensor of claim 1, wherein in step (2), a ratio of the carboxylated upconversion nanomaterial to the 1-ethyl-(3-dimethylaminopropyl) carbodiimide hydrochloride aqueous solution to the N-hydroxysulfosuccinimide aqueous solution to the solution of the complementary chain is 20 mg: 1 mL: 1 mL: 60 μL; and the complementary chain consists of a sequence shown as
5'-GCATGCCTTAAGC-
GATCGGGGGGCCGTCCGGTGCCGAACC-
CAACCAGGGT
GACGCGCACCTAGGCTCGAGGTGCAC-$C_6$—
$NH_2$-3' (SEQ ID NO:2).

3. The flexible paper-based sensor of claim 1, wherein in step (3), a ratio of 2-aminoterephthalic acid to $Fe(NO_3)_3 \cdot 9H_2O$ to N,N-dimethylformamide is (0.9-1.0) g:(2.0-2.1) g: 50 mL;

a ratio of the $NH_2$-MIL-53(Fe) to $CuCl_2$ to the deionized water is 50 mg: 1 g: 10 mL;

a ratio of the $NH_2$-MIL-53(Fe)@$Cu^{2+}$ to the glutaraldehyde solution to the PBS to the tetracycline aptamer is 10 mg: 1.25 mL: 5 mL: 30 μL;

the tetracycline aptamer consists of a sequence shown as
5'-$NH_2C_6$-CGTACGGAAT-
TCGCTAGCCCCCCGGCAGGC- CACGGCTTGGGTTGGTCCCAC TGCGCGTGGATCCGAGCTCCACGTG-3' (SEQ ID NO:1); and
the fifth reaction is carried out in the reactor at 150-160° C. for 7-9 h, and the sixth reaction is carried out for 10-12 h.

4. The flexible paper-based sensor of claim 1, wherein in step (4), a volume ratio of the UCNPs-cDNA signal probe to the Apt-MIL-53(Fe)@$Cu^{2+}$ capture probe is 1:1; a concentration of the UCNPs-cDNA signal probe is 2 mg/mL, and a concentration of the Apt-MIL-53(Fe)@$Cu^{2+}$ capture probe is 1.2 mg/mL; and the mixing is carried out for 15 min.

5. The flexible paper-based sensor of claim 1, wherein in step (5), an addition amount of the detection probe is 3.5 µL; and
the paper-based substrate is prepared through steps of:
ultrasonically mixing ethanol, ammonia water and tetraethyl orthosilicate to obtain a mixed solution, adding a cleaned filter paper to the mixed solution followed by shaking on a shaker, addition of 3-aminopropyltrimethoxysilane, reaction under shaking, washing and drying to obtain a silica-modified filter paper; and subjecting the silica-modified filter paper to hydrophobization to obtain the paper-based substrate.

6. A method for detecting tetracycline residues in a meat product, comprising:
adding a test sample to the flexible paper-based sensor of claim 1, detecting a fluorescence intensity characteristic value of the test sample, and substituting the fluorescence intensity characteristic value into a tetracycline detection standard curve to calculate a tetracycline content in the test sample.

7. The method of claim 6, wherein a linear regression equation of the tetracycline detection standard curve is y=1873.01x−425.34.

* * * * *